United States Patent [19]
Burns et al.

[11] Patent Number: 5,637,574
[45] Date of Patent: Jun. 10, 1997

[54] THERAPEUTIC NUCLEOSIDES

[75] Inventors: Charlene L. Burns, Durham; George W. Koszalka, Chapel Hill; Thomas A. Krenitsky, Chapel Hill; Susan M. Daluge, Chapel Hill, all of N.C.

[73] Assignee: Glaxo Wellcome Inc., Research Triangle Park, N.C.

[21] Appl. No.: 256,308

[22] PCT Filed: Jan. 5, 1993

[86] PCT No.: PCT/GB93/00005

§ 371 Date: Oct. 5, 1994

§ 102(e) Date: Oct. 5, 1994

[87] PCT Pub. No.: WO93/13778

PCT Pub. Date: Jul. 22, 1993

[30] Foreign Application Priority Data

Jan. 6, 1992 [GB] United Kingdom .................. 9200150

[51] Int. Cl.[6] .................... C07H 19/173; A61K 31/70
[52] U.S. Cl. .................... 514/45; 536/27.14; 536/27.61
[58] Field of Search .................... 514/45-46; 536/27.61, 536/27.14

[56] References Cited

U.S. PATENT DOCUMENTS 4,381,344  4/1983  Rideout et al. .................... 435/87

FOREIGN PATENT DOCUMENTS

| 0317128 | 5/1989 | European Pat. Off. . |
| 409227 | 1/1991 | European Pat. Off. . |
| 0129390 | 1/1989 | Japan . |
| WO88/00050 | 1/1988 | WIPO . |

OTHER PUBLICATIONS

Korba et al., "A Cell Culture Assay for Compounds Which Inhibit Hepatitis B Virus Replication," Antiviral Research, 15, 217–228 (1991).

Robinson, "Fields Virology," Edited by Fields et al., vol.2, (1990) Raven Press, New York, Chapters 76 and 77.

Herdewijn et al., "Synthesis and Anti–HIV Activity of Different Sugar–Modified Pyrimidine and Purine Nucleosides," J. Med. Chem., 31, 2040–2048 (1988).

Sells et al., "Replicative Intermediates of Hepatitis B Virus in HepG2 Cells That Produce Infectious Virions," J. Virol., 62(8), 2836 (1988).

Sells et al., "Production of Hepatitis B Virus Particles in Hep G2 Cells Transfected With Cloned Hepatitis B Virus DNA," Proc. Natl. Acad. Sci. USA, 84, 1005–1009 (1987).

Tyle, "Iontophoretic Devices for Drug Delivery," Pharmaceutical Research, 3(6), 318–326 (1986).

Krenitsky et al., "Purine Nucleoside Synthesis, an Efficient Method Employing Nucleoside Phosphorylases," Biochemistry, 20, 3615–3621 (1981).

Southern, "Detection of Specific Sequences Among DNA Fragments Separated by Gel Eletrophoresis," J. Mol. Bio., 98, 503 (1975).

Kowollick et al, "Ein neuer Zugang zu 1–(2, 3–Didesoxy–3–fluor–β–D–ribofuranoayl)–pyrimidinen," J. Prakt. Chem., 315(5), 895–900 (1973).

Etzold et al., "Nucleoside Von Fluorzuckern–V1[1]," Tetrahedron, 27, 2463–2472 (1971).

Montgomery et al., "Synthesis of Potential Anticancer Agents. XXVI. The Alkylation of 6–Chloropurine[2]," J. Amer. Chem. Soc., 83, 630–635 (1961).

Robins et al., "Potential Purine Antagonists. IV. Synthesis of Some 9–Methyl–6–substituted–purines[1]," J. Amer. Chem. Soc., 79. 490–494 (1957).

Schleicher et al, Publication 700 (1987).

Primary Examiner—Gary L. Kunz
Attorney, Agent, or Firm—Donald Brown; Karen L. Prus

[57] ABSTRACT

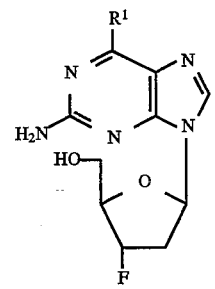

(I)

Compounds or formula (I), wherein $R^1$ represents an n-propoxy, cyclobutoxy, cyclopropylamino, piperidino or pyrrolidino group; or a physiologically functional derivative thereof. The invention further includes methods for the preparation of compounds of formula (I), compositions containing them and the use of these compounds as antiviral agents.

12 Claims, No Drawings

THERAPEUTIC NUCLEOSIDES

This case is a 35 USC 371 stage of PCT/GB93/00005 filed Jan. 5, 1993.

The present invention relates to novel 2',3'-dideoxy-3'-fluoro-purine nucleoside compounds, salts, esters and physiologically functional derivatives thereof, processes for their preparation, pharmaceutical formulations containing them and to their use in therapy, particularly in the treatment or prophylaxis of viral infections.

In the field of antiviral chemotherapy, few drugs exist which effectively combat the virus per se, owing to the difficulty of attacking the virus while leaving uninfected host cells unimpaired. It has been established that certain stages in the virus life-cycle, which vary from species to species, are specified by the virus itself. These stages may prove susceptible to attack where they differ sufficiently from any corresponding host-cell function. However, owing to great similarity between viral and host functions, effective treatments have proved very difficult to identify.

One group of vital pathogens of major consequence worldwide are the hepatitis viruses, in particular, hepatitis B virus (HBV).

HBV is most common in Asian countries and prevalent in sub-Saharan Africa. The virus is etiologically associated with primary hepatocellular carcinoma and is thought to cause 80% of the world's liver cancer. In the United States more than ten thousand people are hospitalised for HBV illness each year, an average of 250 die with fulminant disease. The United States currently contains an estimated pool of 500,000–1 million infectious carriers. Chronic active hepatitis will develop in over 25% of carriers and often progresses to cirrhosis. It is estimated that 5000 people die from HBV-related cirrhosis each year in the U.S.A. and that perhaps 1000 die from HBV-related liver cancer. Even when a universal HBV vaccine is available, the need for effective anti-HBV compounds will continue. The large reservoir of persistently infected carriers, estimated at 220 million worldwide, will receive no benefit from vaccination and will continue to be at high risk for HBV induced liver disease. This carrier population serves as a source of infection for susceptible individuals perpetuating the incidence of disease, particularly in endemic areas or high risk groups, such as drug abusers and homosexuals. Thus, there is a great need for effective antiviral agents, both to control the chronic infection and to reduce progression to hepatocellular carcinoma.

Clinical effects of infection with HBV range from headache to fever, malaise, nausea, vomiting, anorexia and abdominal pains. Replication of the virus is usually controlled by the immune response with a course of recovery lasting weeks or months in humans, but infection may be more severe leading to persistent chronic liver disease as outlined above.

HBV is a small DNA-containing virus which infects humans. It is a member of the class of closely related viruses know as the hepadnaviruses, each member of which selectively infects either mammalian or avian hosts, such as the woodchuck and the duck.

In "Fields Virology" (Volume 2, Ed., Fields et al (1990) Raven Press, New York), Chapters 76 and 77 describe in detail the etiology of hepatitis infections, in particular HBV infections.

Compounds of formula (I) below fall within the scope of the compounds disclosed in European Patent Specification No. 0 317 128. However, there is no specific disclosure of the compounds of formula (I) or of their use in medical therapy.

We have now surprisingly and unexpectedly found that the compounds of formula (I) below are suitable for use in the treatment or prophylaxis of hepatitis viral infections, especially HBV.

According to a first aspect of the present invention there is provided a compound of formula (I):

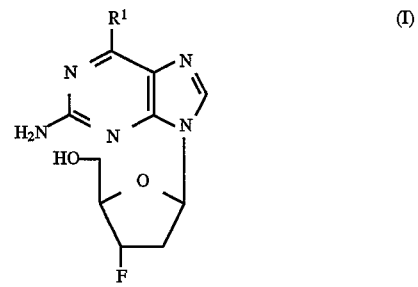

wherein $R^1$ represents an n-propoxy, cyclobutoxy, cyclopropylamino, piperidino, or pyrrolidino group; or a salt, ester or physiologically functional derivative of a compound of formula (I) or a solvate of any thereof.

The compounds of formula (I) may be named as follows:
(1) 2-Amino-9-(2,3-dideoxy-3-fluoro-β-D-erythro-pentofuranosyl)-6-n-propoxy-9H purine;
(2) 2-Amino-6-cyclobutoxy-9-(2,3-dideoxy-3-fluoro-β-D-erythro-pentofuranosyl)-9H-purine;
(3) 2-Amino-6-(cyclopropylamino)-9-(2,3-dideoxy-3-fluoro-β-D-erythropentofuranosyl)-9H-purine;
(4) 2-Amino-6-(1-piperidino)-9-(2,3-dideoxy-3-fluoro-β-D-erythro-pentofuranosyl)-9H-purine; and
(5) 2-Amino-6-(1-pyrrolidino)-9-(2,3-dideoxy-3-fluoro-β-D-erythropentofuranosyl)-9H-purine.

Especially preferred compounds of formula (I) are 2-amino-6-(cyclopropylamino)-9-(2,3-dideoxy-3-fluoro-β-erthro-pentofuranosyl)-9H-purine and 2-amino-6-(1-pyrrolidino)-9-(2,3-dideoxy-3-fluoro-β-D-erythropentofuranosyl)-9H-purine. These compounds are of particular use against HBV infections of animals, which term is intended to include humans, woodchucks and ducks.

The terms piperidino and pyrrolidino are used herein to refer respectively to piperidinyl and pyrrolidinyl groups substituted at the 1-position.

The compounds of formula (I) above and their physiologically functional derivatives are hereinafter referred to as the compounds according to the invention.

The present invention also provides compounds according to the invention for use in therapy, more particularly for use as an antiviral agent, for example, for use in the treatment or prophylaxis of a hepatitis infection, such as an HBV infection.

Further aspects of the present invention include:
a) A method for the treatment or prevention of the symptoms or effects of a viral infection in an infected animal, for example, a mammal including man, which comprises treating said animal with a therapeutically effective amount of a compound according to the invention. According to a particular embodiment of this aspect of the invention, the viral infection is an HBV infection.
b) A method for the prophylaxis of a viral infection, particularly an HBV infection in an animal, for example, a mammal including man which comprises treating said animal with a therapeutically effective amount of a compound according to the invention.
c) Use of a compound according to the invention for the manufacture of a medicament for the treatment or prophylaxis of a viral infection, in particular an HBV infection.

As used herein, the term "physiologically functional derivative" means any physiologically acceptable salt, ester, or salt of such ester, of a compound of formula (I) or a compound which upon administration to the recipient is capable of providing (directly or indirectly) such a compound or an antivirally active metabolite or residue thereof. For example, it is within the scope of the invention to replace the H of the OH group at the 5'-position by a potentially hydrolysable group such as acyl or alkyl.

Preferred esters of the compounds of formula (I) included within the scope of the invention as physiologically functional derivatives include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); amino acid esters (for example, L-valyl or L-isoleucyl); and mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises an optionally substituted phenyl group. Any reference to any of the above compounds also includes a reference to a physiologically acceptable salt thereof.

Examples of physiologically acceptable salts of the compounds of formula (I) and physiologically acceptable derivatives thereof include salts derived from an appropriate base, such as an alkali metal (for example, sodium), an alkaline earth metal (for example, magnesium), ammonium and $NX_4^+$ (wherein X is $C_{1-4}$alkyl). Physiologically acceptable salts of an hydrogen atom or an amino group include salts of organic carboxylic acids such as acetic, lactic, tartaric, malic, isethtonic, lactobionic and succinic acids; organic sulfonic acids such as methanesulphonic, ethanesulphonic, benzenesulphonic and p-toluenesulphonic acids and inorganic acids such as hydrochloric, sulphuric, phosphoric and sulphamic acids. Physiologically acceptable salts of a compound having an hydroxy group consist of the anion of said compound in combination with a suitable cation such as $Na^+$, $NH_4^+$, and $NX_4^+$ (wherein X is a $C_{1-4}$alkyl group).

For therapeutic use, salts of compounds of formula (I) will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived from a physiologically acceptable acid or base, are within the scope of the present invention.

The compounds according to the invention may be employed alone or in combination with other therapeutic agents for the treatment of the above infections or conditions. Combination therapies according to the present invention comprise the administration of at least one compound of the formula (I) or a physiologically functional derivative thereof and at least one other pharmaceutically active ingredient. The active ingredient(s) and pharmacologically active agents may be administered together or separately and, when administered separately this may occur simultaneously or sequentially in any order.

The amounts of the active ingredient(s) and pharmacologically active agent(s) and the relative timings of administration will be selected in order to achieve the desired combined therapeutic effect. Preferably the combination therapy involves the administration of one compound of the formula (I) or a physiologically functional derivative thereof and one of the agents mentioned herein below.

Examples of such further therapeutic agents which are effective for the treatment of HBV infections include carbovir, oxathiolan nucleoside analogues such as cis-1-(2-hydroxymethyl)-1,3-oxathiolan-5-yl)cytosin or cis-1-(2-hydroxymethyl)-1,3-oxathiolan-5-yl)-5-fluoro-cytosine, 2',3'-dideoxy-5-ethynyl-3'-fluorouridine, 5-chloro-2',3'-dideoxy-3'-fluourouridine, 1-(β-D-arabinofuranosyl)-5-propynyluracil, acyclovir and interferons, such as α-interferon.

More preferably the combination therapy involves the administration of one of the above-mentioned agents together with one of the compounds of formula (I) specifically named herein.

The present invention further provides pharmaceutical formulations of the compounds according to the invention, also referred to herein as active ingredients, which may be administered for therapy to a mammal including a human ("the recipient") by any suitable route appropriate to the clinical condition to be treated; suitable routes include oral, rectal, nasal, topical (including buccal, sublingual and transdermal), vaginal and parenteral (including subcutaneous, intramuscular, intravenous and intradermal). It will be appreciated that the preferred route will vary with the condition, weight, age and sex of the recipient, the nature of the infection and the chosen active ingredient.

The amount of a compound of the invention required for the treatment of viral infections, including HBV infections will depend on a number of factors including the severity of the condition to be treated and the identity of the recipient and will ultimately be at the discretion of the attendant physician.

In general, a suitable dose for the treatment of a viral infection, such as, HBV is in the range 0.5 to 120 mg per kilogram body weight of the recipient per day, preferably in the range 1 to 90 mg per kilogram body weight per day and most preferably in the range 2 to 60 mg per kilogram body weight per day. An optimum dose is about 10 mg per kilogram body weight per day. Unless otherwise indicated all weights of active ingredients are calculated as the parent compounds of formula (I). In the case of a physiologically acceptable salt, ester or other physiologically functional derivative of a compound of formula (I) or a solvate of any thereof the figures would be increased proportionately. The desired dose is preferably presented as two, three, four, five, six, or more sub-doses administered at appropriate intervals throughout the day. These sub-doses may be administered in unit dosage forms, for example, containing from 1 to 1500 mg, preferably from 5 to 1000 mg, most preferably from 10 to 700 mg of active ingredient per unit dosage form. Alternatively, if the condition of the recipient so requires, the dose may be administered as a continuous infusion.

Ideally, the active ingredient should be administered to achieve peak plasma concentrations of the active compound of from about 0.25 to about 100 μM, preferably from about 0.5 to 70 μM, most preferably from about 1 to about 50 μM. This may be achieved, for example, by the intravenous injection of a 0.1 to 5% w/v solution of the active ingredient, optionally in saline, or orally administered, for example, as a tablet, capsule, or syrup containing from about 0.5 to about 100 mg/kg of the active ingredient. Desirable blood levels may be maintained by a continuous infusion to provide from about 0.01 to about 5.0 mg/kg/hour or by intermittent infusions containing from about 0.4 to about 15 mg/kg of the active ingredient.

While it is possible for the active ingredient to be administered alone, it is preferable to present it as a pharmaceutical formulation. The formulations of the present invention comprise at least one active ingredient, as defined above, together with one or more acceptable carriers thereof and, optionally, one or more other therapeutic agents. Each carrier must be "acceptable" in the sense of being compatible with the other ingredients of the formulation and not injurious to the patient.

Formulations of the invention include those suitable for administration by any of the aforementioned routes which may conveniently be presented in unit dosage form and may be prepared by any method well know in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers, or both, and then, if necessary, shaping the product.

Formulations of the present invention suitable for oral administration may be presented as discrete units such as capsules, cachets or tablets each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented as a bolus, electuary, or paste or may be contained within liposomes.

A tablet may be made by compression or moulding, optionally with one or more accessory ingredients. Compressed tablets may be prepared by compressing in a suitable machine the active ingredient in a free-flowing form such as a powder or granules, optionally mixed with a binder (for example, povidone, gelatin, hydroxypropylmethyl cellulose), lubricant, inert diluent; preservative, disintegrant (for example, sodium starch glycollate, cross-linked povidone, crossed-linked sodium carboxmethyl cellulose), or a surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile or to be soluble or effervescent when added to liquid. Tablets may optionally be provided with an enteric coating, to provide release in parts of the gut other than the stomach.

Formulations suitable for oral use may also include buffering agents designed to neutralise stomach acidity. Such buffers may be chosen from a variety of organic or inorganic agents such as weak acids or bases admixed with their conjugated salts.

A capsule may be made by filling a loose or compressed powder on an appropriate filling machine, optionally with one or more additives. Examples of suitable additives include binders such as povidone; gelatin, lubricants, inert diluents and disintegrants as for tablets. Capsules may also be formulated to contain pellets or discrete sub-units to provide slow or controlled release of the active ingredient. This can be achieved by extruding and spheronising a wet mixture of the drug plus an extrusion aid (for example microcrystalline cellulose) plus a diluent such as lactose. The spheroids thus produced can be coated with a semipermeable membrane (for example ethyl cellulose, Eudragft WE30D) to produce sustained release properties.

An edible foam or whip formulation ideally comprises; 50–70% of an edible oil, particularly a vegetable oil, including corn oil, peanut oil, sunflower oil, olive oil and soybean oil; 2–10% of one or more surfactants particularly lecithin, polyols, polyol polymer esters including glyceryl fatty acid esters, polyglyceryl fatty acid esters (e.g. decaglycerol tetraoleate), or sorbitan fatty acid esters (e.g. sorbitan monostearate); 1–4% of a propellant which is suitable for ingestion, notably a compressed gas propellant especially nitrogen, nitrous oxide or carbon dioxide, or a gaseous hydrocarbon especially propane, butane or isobutane; 0.5–30% of one or more viscosity modifiers of particle size in the range 10–50 microns in diameter, particularly powdered sugars or colloidal silicon dioxide; and optionally 0.5–1% of one or more suitable, non-toxic colourings, flavourings or sweetners. The active ingredient is preferably present in such formulations in a concentration of 10–46%, advantageously 30%. An edible foam or whip formulation as described above may be prepared in a conventional manner, for example by mixing the edible oil, surfactant(s) and any other soluble ingredients, adding the viscosity modifier(s) and milling the mixture to form a uniform dispersion and suspension. The active ingredient is blended into the milled mixture until evenly dispersed. Finally, a metered quantity of propellant is incorporated to the mixture after said mixture has been measured into a suitable dispensing container.

Pharmaceutical formulations for topical administration according to the present invention may be formulated as an ointment, cream, suspension, lotion, powder, solution, paste, gel, spray, aerosol or oil. Alternatively, a formulation may comprise a dressing such as a bandage or adhesive plaster impregnated with active ingredients and optionally one or more excipients or diluents.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution of 2) dissolved in an adhesive or 3) dispersed in a polymer. A suitable concentration of the active compound is about 1% to 20%, preferably about 3% to 15%. As one particular possibility, the active compound may be delivered from the patch by iontophoresis as generally described in Pharmaceutical Research, 3(6), 318 (1986).

For infections of the eye or other external tissues, for example mouth and skin, the formulations are preferably applied as a topical ointment or cream containing the active ingredient in an amount of, for example, 0.075 to 20% w/w, preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base or as a water-in-oil base.

If desired, the aqueous phase of the cream base may include, for example, at least 40–45% w/w of a polyhydric alcohol, i.e. an alcohol having two or more hydroxyl groups such as propylene glycol, butane-1,3-diol, mannitol, sorbitol, glycerol and polyethylene glycol and mixtures thereof. The topical formulations may include a compound which enhances absorption or penetration of the active ingredient through the skin or other affected areas. Examples of such dermal penetration enhancers include dimethylsulphoxide and related analogues.

The oily phase of an emulsion formulation according to the invention may comprise merely an emulsifier (otherwise known as an emulgent), but desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifer(s) with or without stabilizer(s) make up the so-called emulsifying wax, and the wax together with the oil and/or fat make up the so-called emulsifying ointment base which forms the oily phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent. The ingredient is preferably present in such formulations in a concentration of 0.5 to 20%, advantageously 0.5 to 10%, particularly about 1.5% w/w.

Formulations suitable for topical administration in the mouth include lozenges comprising the active ingredient in a flavoured material, usually sucrose and acacia or tragacanth; pastilles comprising the active ingredient in an inert material such as gelatin and glycerin, or sucrose and acacia; and mouth-washes comprising the active ingredient in a suitable liquid carrier.

Formulations for rectal administration may be presented as a suppository with a suitable base comprising for example cocoa butter or higher fatty alcohol (e.g. hard wax, European Pharmacopoeia) or triglycerides and saturated fatty acids (e.g. Witepsol).

Formulations suitable for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or sub-dose, as herein above recited, or an appropriate fraction thereof, of an active ingredient.

It should be understood that in addition to the ingredients particularly mentioned above, the formulations of this invention may include other agents conventional in the art having regard to the type of formulation in question, for example those suitable for oral administration may include flavouring agents.

The present invention further includes a process for the preparation of a compound of formula (I) or a salt, ester or physiologically functional derivative of a compound of formula (I) or a solvate of any thereof which comprises either:

(A) reacting a purine base of formula (II)

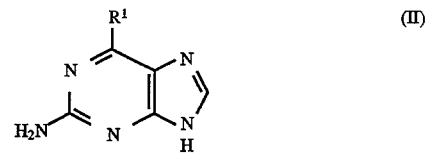

wherein $R^1$ is as hereinbefore defined, or a functional equivalent thereof, with a compound of formula (III)

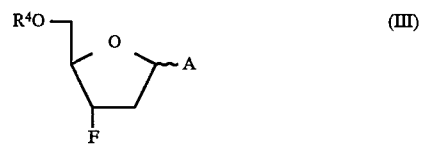

wherein $R^4$ represents hydrogen or a hydroxy protecting group and A is a phosphate group or salt thereof or a purine or pyrimidine moiety other than (II) or a leaving group, to form a compound of formula (I); or (B) reacting a compound of formula (IV)

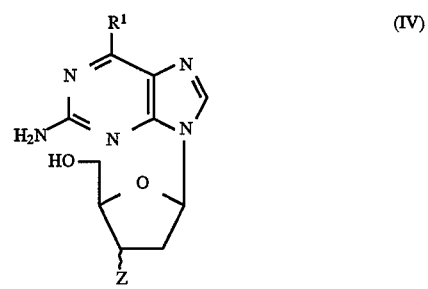

wherein $R^1$ is as hereinbefore defined and Z represents a precursor group for the fluoro atom, with agent(s) and/or under conditions serving to convert the precursor group Z to a fluoro atom in the erythro configuration;

and thereafter, or simultaneously therewith, effecting one or more of the following optional conversions:

(i) removing any remaining protecting group(s);

(ii) when a compound of formula (I) is formed, converting it into a salt, ester or physiologically functional derivative of a compound of formula (I); or (iii) when a salt, ester or physiologically functional derivative of a compound of formula (I) or a solvate of any thereof is formed, converting the derivative into a compound of formula (I) or into a different derivative of the compound of formula (I).

In the above-described process according to the invention, the starting compounds of formulae (II), (III) and (IV), as well as the above-mentioned agents and conditions, may be selected from those which are known in the art of nucleoside synthetic chemistry. Examples of such conversion procedures are described hereinafter for guidance and it will be understood that they may be modified in conventional manner depending on the desired compound of formula (I). In particular, where a conversion is described which would otherwise result in the undesired reaction of labile groups, then such groups may be protected in conventional manner with subsequent removal of the protecting group(s) after completion of the conversion.

According to the conditions employed to effect process A, the purine base of formula (II) and the compound of formula (III) may or may not be protected using conventional protecting groups, such as acyl groups, for example, alkanoyl (for example, acetyl), substituted alkanoyl, such as alkoxyalkanoyl, aroyl (for example, benzoyl), ether groups, for example, trialkylsilyl groups, such as t-butyldimethylsilyl or other groups, such as aralkyl (for example, benzyl) or a phosphate group.

Such groups may be removed by acid or base hydrolysis, hydrogenolysis, or enzymatically. Acyl groups are typically removed by base hydrolysis and silyl groups by acid hydrolysis or fluoride ion. Aralkyl groups such as benzyl are advantageously removed by catalytic hydrogenolysis.

Two methods are commonly employed to effect process A, viz enzymatic and chemical.

Process (A) may be effected enzymatically by, for example, reacting an appropriate purine base of formula (II), wherein $R^1$ is as hereinbefore defined, or a functional equivalent of any thereof, for example, a salt or protected derivative thereof (see above), with a compound of formula (III) wherein $R^4$ is hydrogen or a hydroxy protecting group (see above) and A is a purine or pyrimidine moiety (other than (II)), a phosphate group or a salt thereof.

In the case where A is a purine or pyrimidine derivative (other than (II)), the reaction may be carried out in the presence of (i) phosphorylase enzymes, such as purine nucleoside phosphorylase and thymidine phosphorylase and an in organic phosphate or salt thereof, or (ii) a transferase enzyme, for example, N-deoxyribosyl transferase. In order to obtain the compounds of the invention it is necessary when employing this method that the compound of formula (III) should be in its β-form.

Purine nucleoside phosphorylase and thymidine phosphorylase may be prepared by the methods described in Krenitsky et al., *Biochemistry*, 20, 3615-, 1981 and U.S. Pat. No. 4,381,344.

The N-deoxyribosyl transferase may be isolated by standard biochemical techniques from:

(i) *E. coli* strain SS6030/14 which expresses lactobacillus enzyme, available from the American Type Culture Collection (ATCC) Rockville, Md. 20852-1776 from 18th Jul., 1990 under Accession No. ATCC 68367, or (ii) *E. coli* strain SS70-8/15 which expresses lactobacillus enzyme, available from the ATCC from 17th Jun., 1992 under Accession No. ATCC 69016.

In the case where A represents a phosphate group or a salt thereof, the reaction may be carried out in the presence of a single phosphorylase enzyme, such as purine nucleoside phosphorylase. In order to obtain the compounds of the invention it is necessary when employing this method that the compound of formula (III) should be in its α-form.

Protecting groups may be used in the enzymatic process but in practice have been found to be unnecessary and in some cases to be actually disadvantageous in terms of overall yield.

Process (A) may be effected chemically by, for example, reacting a compound of formula (II) as hereinbefore defined with a compound of formula (III) wherein $R^4$ is hydrogen or a hydroxy protecting group and A represents a suitable leaving group, such as a halogen atom, for example, chlorine, an acyloxy group, such as acetoxy or an alkoxy group, for example, methoxy, in the presence of a catalyst, such as tin (IV) chloride or trimethylsilyltriflate, in a suitable solvent, such as acetonitrile.

In contrast to the enzymatic method it has been found that in the chemical process (a) the compounds of formula (II) and (III) may advantageously be protected (vide supra) and (b) the compound of formula (I) so formed is a mixture of α- and β-anomers. The β-anomers of the present invention may be obtained by anomeric separation by methods well known to a skilled person or readily available in the chemical literature, for example, by silica gel column chromatography or HPLC.

Compounds of formula (II) wherein $R^1$ is as hereinbefore defined or a functional equivalent of any thereof may be obtained commercially, for example, from the Aldrich Chemical Company or prepared by conventional methods well known to a skilled person or readily available from the chemical literature, for example, by methods the same as or analogous to those described in Robins et al., J. Amer. Chem. Soc. 1957, 79, 490–494 and Montgomery and Temple, J. Amer. Chem. Soc., 1961, 83, 630–635.

For example, the appropriate purine base may be prepared from a corresponding purine wherein the 6-substituent is a suitable leaving group, for example, chlorine, by nucleophilic displacement of said group. Thus purines wherein the 6-substituent is propoxy or cyclobutoxy may be prepared by treatment of the corresponding 6-chloropurine with propanol or cyclobutanol respectively, in the presence of a base such as sodium hydride, and purines wherein the 6-substituent is cyclopropylamino, piperidinyl, or pyrrolidinyl may be prepared by treatment of the corresponding 6-chloropurine with the appropriate amine, viz. cyclopropylamine, piperidine, or pyrrolidine respectively, in a suitable solvent.

The 2-amino-6-chloro purine precursor may be obtained commercially (Aldrich Chemical Co.) or prepared by methods well known to a skilled person or readily available from the chemical literature.

Compounds of formula (III) wherein A is a pyrimidine or purine moiety may conveniently be prepared by methods well known to a skilled person or readily available from the chemical literature. For example, 2',3'-dideoxy-3'-fluorouridine may be obtained commercially or prepared by the method described in A. Kowollick et al., J. Prakt. Chem. 1973, 315(5), 895, 3'-deoxy-3'-fluorothymidine may be prepared by the method described by Etzold et al., Tetrahedron, 1971, 27, 2463–2472 and 2',3'-dideoxy-3'-fluoroguanine may be prepared by the method of Herdewijne et al., J. Med. Chem., 1988, 31, 2040–2048.

Compounds of formula (III) wherein A represents a phosphate group may be prepared chemically by methods analogous to those available in the chemical literature or from compounds of formula (III) wherein A is a pyrimidine or purine moiety by treatment with a phosphorylase enzyme, such as thymidine phosphorylase.

Compounds of formula (III) wherein $R^4$ is as hereinbefore defined and A represents a leaving group, such as methoxy, may be obtained commercially or may be prepared according to the method of Asahi Glass as described in Japanese Patent Application No. JP0129390.

With regard to process (B), this may be effected, for example, by treatment of a compound of formula (IV) in which Z represents a leaving group, for example, hydroxy or an organosulphonyloxy, such as methanesulphonyloxy or trifluoromethanesulphonyloxy, with an appropriate fluorinating agent, such as diethylaminosulphurtrifluoride, potassium fluoride, potassium hydrogen fluoride, or tetra-n-butylammonium fluoride.

Compounds of formula (IV) may be prepared by methods well known to a skilled person or readily available from the chemical literature, for example, by the method of Herdewijn et al., J. Med-Chem., 1988, 31, 2040–2048.

Esters according to the invention may be prepared by methods known in the art. For example, by treatment of the parent compound of formula (I) with an appropriate esterifying agent, for example, by treatment with an appropriate acid halide, for example, chloride or anhydride.

A compound of formula (I) may be converted into a corresponding physiologically acceptable ether of formula (I) by reaction with an appropriate alkylating agent in a conventional manner.

The compounds of formula (I), including esters thereof, may be converted into physiologically acceptable salts in a conventional manner, for example, by treatment with an appropriate base. An ester or salt of a compound of formula (I) may be converted into the parent compound by, for example, hydrolysis.

The following Examples are intended for illustration only and are not intended to limit the scope of the invention in any way. The term 'active ingredient' as used in the Examples means a compound of formula (I) or a salt, ester or physiologically functional derivative of a compound of formula (I) or a solvate of any thereof.

EXAMPLE 1

2-Amino-9-(2,3-dideoxy-3-fluoro-β-D-erythropentofuranosyl)-6-n-propoxy-9H-purine 2-Amino-6-n-propoxy-9H-purine was prepared by displacement of the chlorine group on 2-amino-6-chloropurine (Aldrich Chemical Company) by propanol (Aldrich Chemical Company) in the presence of sodium hydride. 2-Amino-6-n-propoxy-9H-purine (0.50 g, 2.6 mmoles) was dissolved in dimethylformamide (5 ml, DMF) and dimethylsulphoxide (5 ml, DMSO). 3'-Deoxy-3'-fluorothymidine (0.76 g, 3.1 mmoles) and 30 ml 10 mM potassium phosphate buffer, pH 6.8, containing 0.04% potassium azide were added. Purified purine nucleoside phosphorylase (7,500 I.U.) and thymidine phosphorylase (3750 I.U.) adsorbed onto 5 ml DEAE-cellulose resin were added to the reaction mixture and the suspension stirred at 37° C. After 24 days, the reaction was filtered and the filtrate applied to a series of coupled columns. The initial column contained AG1-X2 (OH-form, 2.5×10 cm) while the second column contained Amberlite XAD-2 resin (2.5×20 cm). After sample application, the columns were washed with water (500 ml) and the product eluted with methanol. Product-containing fractions were then flash chromatographed down a silica gel column (4.8× 20 cm) using dichloromethane:methanol (95:5) as eluant. Solvent was evaporated in vacuo and lyophilisation yielded 0.46 g of 2-amino-9-(2,3-dideoxy-3-fluoro-β-D-erythropentofuranosyl)-6-propoxy-9H-purine (56%): mp 128° C.;

TLC Rf 0.85 (silica gel, MeCN:15N $NH_4OH:H_2O$/ 85:5:10);

$[\alpha]_D$ –37.2 (c=0.5, DMF);

UV $\lambda_{max}$ ($\epsilon \times 10^{-3}$) at pH 7, 280 (9.9) and 247.5 (10.3); at pH 13, 279.5 (10.6) and 247.5 (10.6);

$^1$H NMR (200 MHz, DMSO-$d_6$) δ8.07 (s,1H,$H_8$), 6.41 (b,2H,$NH_2$), 6.23 (dd,1H,$H_{1'}$,J=9.1 Hz,J=5.7 Hz), 5.37 (dd, 1H,$H_{3'}$,J=53.8 Hz,J=4.2 Hz), 5.19 (t,1H,$OH_{5'}$,J=5.6 Hz), 4.34 (t,2H,J=6.8 Hz,$OCH_2CH_2CH_3$), 4.16 (dt,1H,$H_{4'}$,J=27.0 Hz,J=4.9 Hz), 3.56 (m,2H,$H_{5'}$ and $H_{5''}$), 2.94 and 2.68 (2m,2H total, $H_{2'}$ and $H_{2''}$), 1.73 (m,2H,$OCH_2CH_2CH_3$), and 0.95 (t,3H,J=7.4 Hz, $OCH_2CH_2CH_3$);

MS (ci) 312 (M+1), 293 (M-F), 194 ($MH_2$—$C_5H_8FO_2$).

Anal. ($C_{13}H_{18}FN5O_3.0.16H_2O$) C,H,F,N. Calculated: C,49.70; H,5.88; F,6.05; N,22.29 Found: C,49.58 H,5.90 F,6.30 N,22.04

EXAMPLE 2

2-Amino-6-cyclobutoxy-9-(2,3-dideoxy-3-fluoro-β-D-erythropentofuranosyl)-9H-purine 2-Amino-6-cyclobutoxy-9H-purine was prepared by displacement of the chlorine group on 2-amino-6-chloropurine (Aldrich Chemical Company), by cyclobutanol (Aldrich Chemical Company) in the presence of sodium hydride.

2-Amino-6-cyclobutoxy-9H-purine (0.50 g, 2.4 mmoles) and 2'3'-dideoxy-3'-fluorouridine (0.67 g, 2.9 mmoles) were suspended in potassium phosphate buffer (50 ml, 10 mM), pH 7.0, containing 0.04% potassium azide. Purine nucleoside phosphorylase (1120 I.U.) and thymidine phosphorylase (10,000 I.U.) immobilized on DEAE cellulose was added to the reaction and the suspension was stirred at 45° C. After 8 days, MeOH (150 ml) was added to the reaction. The reaction was applied to a column containing AG1-X2 (OH⁻ form, 2.5×10 cm) and eluted with MeOH. Fractions containing product were pooled, concentrated, and flash chromatographed on silica gel (2.5×20 cm) with dichloromethane:acetone (92:8) as eluant. Solvent was removed and lyophilization yielded 0.57 g of 2-amino-6-cyclobutoxy-9-(2,3-dideoxy-3-fluoro-β-D-erythropentofuranosyl)-9H-purine (70%): mp 139°–140° C.;

TLC Rf 0.75 (silica gel, MeCN:15N $NH_4OH:H_2O$/ 85:5:10);

$[\alpha]_D^{20}$ –17.2° C. (c=0.5, DMF);

UV $\lambda_{max}$ ($\epsilon \times 10^{-3}$) at pH 7, 281 (9.5) and 247 (9.4); at pH 13, 281 (9.9) and 247 (9.5);

$^1$H NMR (400 MHz, DMSO-$d_6$) δ8.08 (s, 1H, $H_8$), 6.40 (s, 2H, $NH_2$), 6.22 (dd, 1H, $H_{1'}$, J=9.4 Hz, J=5.5 Hz), 5.38 (dd, 1H, $H_{3'}$, J=53.6 Hz, J=4.0 Hz), 5.26–5.30 (m, 1H, OCH), 5.19 (t, 1H, $OH_{5'}$, J=5.6 Hz), 4.16 (dt, 1H, $H_{4'}$, J=26.8 Hz, J=4.8 Hz), 3.55 (t, 2H, $H_{5'}$ and $H_{5''}$, J=5.3 Hz), 2.78–2.96 and 2.52–2.64 (m, 2H, $H_{2'}$ and $_{2''}$) and 2.36–2.45, 2.05–2.16, 1.74–1.83, and 1.55–1.67 (4m, 6H, cyclobutyl protons);

MS (ci) 324 (M+1), 304 (M-F), 206 ($MH_2$—$C_5H_8FO_2$). Elemental Analysis for $C_{14}H_{18}FN_5O_3.0.65H_2O$ Calculated: C,50.19; H,5.81; F,5.67; N,20.90 Found: C,50.27; H,5.74; F,5.62; N,20.77

EXAMPLE 3

2-Amino-6-(cyclopropylamino)-9-(2,3-dideoxy-3-fluoro-β-D-erythropentofuranosyl)-9H-purine 2-Amino-6-(cyclopropylamino)-9H-purine was prepared by the displacement of the clorine group on 2-amino-6- chloropurine (Aldrich Chemical Company) by cyclopropylamine (Aldrich Chemical Company) 2-Amino-6-(cyclopropylamino)-9H-purine (0.50 g, 2.7 mmoles) was dissolved in DMF (5 ml) and DMSO (5 ml). 3'-Deoxy-3'-fluorothymidine (0.81 g, 3.3 mmoles) and potassium phosphate buffer (10 mM, 30 ml), pH 6.8, containing 0.04% potassium azide were added. Purified purine nucleoside phosphorylase (7500 I.U.) and thymidine phosphorylase (37.50 I.U.) adsorbed onto 5 ml DEAE-cellulose resin were added to the reaction and the suspension stirred at 37° C. After 23 days, the reaction was filtered and the filtrate applied to a series of coupled columns. The initial column contained AG1-X2 (OH-form, 2.5×10 cm) while the second column contained Amberlite XAD-2 resin (2.5×20 cm). After sample application, the columns were washed with water (700 ml) and the product eluted with methanol. Product-containing fractions were then flash chromatographed down a silica gel column (4.8×24 cm) using ethyl acetate:methanol (95:5) as eluant. The product was further purified by flash chromatography down a silica gel column (2.5×40 cm) using dichloromethane:methanol(9:1) as eluant. Solvent was evaporated in vacuo and lyophilisation yielded 0.30 g of 2-amino-6-(cyclopropyl-amino)-9-(2,3-dideoxy-3-fluoro-β-D-erythro-pentofuranosyl)-9H-purine (33%): mp 75° C.;

TLC Rf 0.66 (silica gel, MeCN:15N NH$_4$OH:H$_2$O/ 85:5:10);

$[\alpha]_d$ –26.4 (c=0,5,DMF);

UV $\lambda_{max}$ ($\varepsilon \times 10^{-3}$) at pH 7,283 (13.7) and 261 (9.2); at pH 13, 283 (13.8) and 261 (9.3);

$^1$H NMR (300 MHz, DMSO-d$_6$) δ7.93 (s1H,H$_8$), 7.44(d, 1H,NH,J=3.8 Hz), 6.22 (dd,1H,H$_{1'}$, J=9.4 Hz,J=5.6 Hz), 5.85(b,2H,NH$_2$), 5.52(t,1H, OH$_{5'}$,J=5.9 Hz), 5.40(dd,1H, H$_{3'}$, J=54.1 Hz,J=4.4 Hz), 4.19 (dt,1H,H$_4$, J=27.5 Hz,J=4.3 Hz), 3.60 (apparent triplet, 2H,H$_{5'}$ and H$_{5''}$,J=5.1 Hz), 2.97, 2.81 and 2.58 (3m,3H total, H$_{2'}$,H$_{2''}$, and CH$_2$CH$_2$CH) and 0.66 and 0.58 (2m,4H,CH$_2$CH$_2$CH);

MS (ci) 309 (M+1), 289 (M-F), 191 (MH$_2$—C$_5$H$_8$F—O$_2$).

Anal. (C$_{13}$H$_{17}$FN$_6$O$_2$.0.6H$_2$O.0.3C$_2$H$_6$O) C,H,F,N. Calculated: C,49.06; H,6.05; F,5.71; N,25.24 Found: C,49.06 H,5.84 F,5.97 N,25.00

EXAMPLE 4

2-Amino-6-(1-piperidino)-9-(2,3-dideoxy-3-fluoro-β-D-erythropentofuranosyl)-9H-purine 2-Amino-6-(1-piperidino)-9H-purine was prepared by displacement of the chlorine group on 2-amino-6-chloropurine (Aldrich Chemical Company) by piperidine (Aldrich Chemical Company).

2-Amino-6-(1-piperidino)-9H-purine (0.60 g, 2.7 mmoles) and 2',3'-dideoxy-3'-fluorouridine (0.50 g, 2.2 mmoles) were suspended in potassium phosphate buffer (50 ml, 10 mM), pH 7.0, containing 0.04% potassium azide. Purine nucleoside phosphorylase (1120 I.U.) and thymidine phosphorylase (10,000 I.U. (Krenitsky, et al., Biochemistry, 20, 3615, 1981 and U.S. Pat. No. 4,381,344) immobilized on DEAE cellulose was added to the reaction and the suspension was stirred at 45° C. After 3 days, methanol (100 ml) was added to the reaction. The reaction was applied to a column containing AG1-X2 (OH-form, 2.5×10 cm) and eluted with MeOH. Fractions containing product were pooled, concentrated, and flash chromatographed on silica gel (2.5×20 cm) with dichloromethane:acetone (9:1) as eluant. Solvent was removed and lyophilization yielded 0.41 g of 2-amino-6-(1-piperidino)-9-(2,3-dideoxy-3-fluoro-β-D-erythropentofuranoxyl)-9H-purine (55%) mp 101°–104° C.;

$[\alpha]_D^{20}$ –15.6(c=0.50, DMF); UV $\lambda_{max}$ ($\varepsilon \times 10^{-3}$) at pH 7,287 (17.6); at pH 13, 287 (17.6);

$^1$H NMR (300 MHz, DMSO-d$_6$) δ7.97 (s, 1H, H$_8$), 6.26 (dd, 1H, H$_{1'}$, J=9.4 Hz, J=5.6 Hz), 5.86 (b, 2H, NH$_2$), 5.50 (t, 1H, OH$_{5'}$, J=6.0 Hz), 5.40 (m, 1H, H$_{3'}$), 4.25 and 4.14 (2m, 5H, H$_{4'}$, CH$_2$—N—CH$_2$), 3.60 (t, 2H, H$_{5'}$ and H$_{5''}$, J=4.9 Hz), 2.89 and 2.60 (2m, 2H, H$_{2'}$ and $_{2''}$), 1.67 and 1.55 (2m, 6H, (CH$_2$)$_3$);

MS (ci) 337 (M+1), 317 (M-F), 219 (MH$_2$—C$_5$H$_8$FO$_2$).

Elemental Analysis for C$_{15}$H$_{21}$FN$_6$O$_2$.0.35H$_2$O Calculated: C,52.58; H,6.38; F,5.54; N,24.52 Found: C,52.78; H,6.50; F,5.42; N,24.38

EXAMPLE 5

2-Amino-6-(1-pyrrolidino)-9-(2,3-dideoxy-3-fluoro-β-D-erythropentofuranosyl)-9H-purine 2-Amino-6-(1-pyrrolidino)-9H-purine was prepared by displacement of the chlorine group on 2-amino-6-chloropurine (Aldrich Chemical Company), by pyrrolidine (Aldrich Chemical Company).

2-Amino-(1-pyrrolido)-9H-purine (0.59 g, 2.8 mmoles) and 2',3'-dideoxy-3'-fluorouridine (0.50 g, 2.2 mmoles) were suspended in potassium phosphate buffer (50 ml, 10 mM), pH 7.0, containing 0.04% potassium azide. Purine nucleoside phosphorylase (1120 I.U.) and thymidine phosphorylase (10,000 I.U.) (Krenitsky et al., Biochemistry, 20, 3615, 1981 and U.S. Pat. No. 4,381,344) immobilized on DEAE cellulose was added to the reaction and the suspension was stirred at 45° C. After 3 days, methanol (10 ml) was added to the reaction. The reaction was applied to a column containing AG1-X2 (OH-form, 2.5×10 cm) and eluted with MeOH. Fractions containing product were pooled, concentrated, and flash chromatographed on silica gel (2.5×20 cm) with dichloromethane:methanol (97:3) as eluant. Solvent was removed and lyophilization yielded 0.49 g of 2-amino-6-(1-pyrrolidino)-9-(2,3-dideoxy-3-fluoro-β-D-erthro-pentofuranosyl)-9H-purine (68%): mp 101°–104° C.;

$[\alpha]_D^{20}$ –15.2 (c=0.5, DMF);

UV $\lambda_{max}$ ($\varepsilon \times 10^{-3}$) at pH 7,283 (16.0) and 267 (11.4) (sh); at pH 13,284 (16.0) and 266 (11.2) (sh);

$^1$H NMR (300 MHz, DMSO-d$_6$) δ7.94 (s, 1H, H$_8$), 6.26 (dd, 1H, H$_{1'}$, J=9.4 Hz, J=5.6 Hz), 5.82 (b, 2H, NH$_2$), 5.53 (t, 1H, OH$_{5'}$, J=5.6 Hz), 5.42 (dm, 1H, H$_{3'}$, J=53.5 Hz), 4.20 (dm, 1H, H$_{4''}$, J=27.3 Hz), 3.96 (b, 4H 2 CH$_2$) 3.60 (t, 2H, H$_{5'}$ and H$_{5''}$, J=4.9 Hz) 2.90 and 2.55 (m, 2H, H$_{2'}$ and H$_{2''}$), and 1.91 (b, 4H, (CH$_2$)$_2$); MS (ci) 323 (M+1), 303 (M-F), 205 (MH$_2$—C$_5$H$_8$FO$_2$).

Elemental Analysis for C$_{14}$H$_{19}$FN$_6$O$_2$.0.35H$_2$O Calculated: C,51.17; H,6.04; F,5.78; N,25.57 Found: C,51.14; H,5.83; F,5.58; N,25.36

EXAMPLE 6

Tablet Formulations

The following formulations A, B and C are prepared by wet granulation of the ingredients with a solution of povidone, followed by the addition of magnesium stearate and compression.

|   |   | mg/tablet | mg/tablet |
|---|---|---|---|
|   | Formulation A |   |   |
| (a) | Active ingredient | 250 | 250 |
| (b) | Lactose B.P. | 210 | 26 |
| (c) | Povidone B.P. | 15 | 9 |
| (d) | Sodium Starch Glycollate | 20 | 12 |
| (e) | Magnesium Stearate | 5 | 3 |
|   |   | 500 | 300 |
|   | Formulation B |   |   |
| (a) | Active ingredient | 250 | 250 |
| (b) | Lactose | 150 | — |
| (c) | Avicel PH 101 | 60 | 26 |
| (d) | Povidone B.P. | 15 | 9 |
| (e) | Sodium Starch Glycollate | 20 | 12 |
| (f) | Magnesium Stearate | 5 | 3 |
|   |   | 500 | 300 |
|   | Formulation C |   |   |
|   | Active ingredient | 100 |   |
|   | Lactose | 200 |   |
|   | Starch | 50 |   |
|   | Povidone | 5 |   |
|   | Magnesium Stearate | 4 |   |
|   |   | 359 |   |

The following formulations, D and E, are prepared by direct compression of the admixed ingredients. The lactose in formulation E is of the direct compression type (Dairy Crest—"Zeparox").

|   | mg/tablet |
|---|---|
| Formulation D |   |
| Active ingredient | 250 |
| Pregelatinised Starch NF15 | 150 |
|   | 400 |
| Formulation E |   |
| Active ingredient | 250 |
| Lactose | 150 |
| Avicel | 100 |
|   | 500 |

Formulation F (Controlled Release Formulation)

The formulation is prepared by wet granulation of the ingredients (below) with a solution of povidone followed by the addition of magnesium stearate and compression.

|   |   | mg/tablet |
|---|---|---|
| (a) | Active ingredient | 500 |
| (b) | Hydroxypropylmethylcellulose (Methocel K4M Premium) | 112 |
| (c) | Lactose B.P. | 53 |
| (d) | Povidone B.P. | 28 |
| (e) | Magnesium Sterate | 7 |
|   |   | 700 |

Drug release takes place over a period of about 6–8 hours and is complete after 12 hours.

EXAMPLE 7

Capsule Formulations
Formulation A

A capsule formulation is prepared by admixing the ingredients of Formulation D in Example 2 above and filling the mixture into a two-part hard gelatin capsule. Formulation B (infra) is prepared in a similar manner.

|   |   | mg/capsule |
|---|---|---|
| Formulation B |   |   |
| (a) | Active ingredient | 250 |
| (b) | Latose B.P. | 143 |
| (c) | Sodium Starch Glycollate | 25 |
| (d) | Magnesium Stearate | 2 |
|   |   | 420 |
| Formulation C |   |   |
| (a) | Active ingredient | 250 |
| (b) | Macrogol 4000 B.P. | 350 |
|   |   | 600 |
| Formulation D |   |   |
|   | Active ingredient | 250 |
|   | Lecithin | 250 |
|   | Arachis oil | 100 |
|   |   | 450 |

Capsules of formulation D are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients (a), (b) and (c) using an extruder, followed by spheronisation of the extrudate and drying. The dried pellets are then coated with the release-controlling membrane (d) and filled into a two-piece, hard gelatin capsule.

|   |   | mg/capsule |
|---|---|---|
| (a) | Active ingredient | 250 |
| (b) | Microcrystalline Cellulose | 125 |
| (c) | Lactose B.P. | 125 |
| (d) | Ethyl Cellulose | 13 |
|   |   | 513 |

EXAMPLE 8

Injectable Formulation

| Formulation A |   |
|---|---|
| Active ingredient | 0.200 g |
| Hydrochloric acid solution, 0.1 m, or Sodium hydroxide solution, 0.1 M q.s. to pH | 4.0 to 7.0 |
| Sterile water q.s. to | 10 ml |

The active ingredient is dissolved in most of the water at 35° C.–40° C. and the pH adjusted to between 4.0 and 7.0 with the hydrochloric acid or sodium hydroxide as appropriate. The batch is then made up to volume with the water and filtered through a sterile micropore filter into a sterile 10 ml amber glass vial (type 1) and sealed with sterile closures and overseals.

| Formulation B | |
|---|---|
| Active ingredient | 0.125 |
| Sterile, pyrogen-free, pH 7 phosphate buffer, q.s. to | 25 ml |

EXAMPLE 9

| Intramuscular injection | |
|---|---|
| Active ingredient | 0.20 g |
| Benzyl Alcohol | 0.10 g |
| Glycofurol 75 | 1.45 g |
| Water for Injection q.s. to | 3.00 ml |

The active ingredient is dissolved in the glycofurol. The benzyl alcohol is then added and dissolved, and water added to 3 ml. The mixture is filtered through a sterile micropore filter and sealed in sterile 3 ml amber glass vials (type 1).

EXAMPLE 10

| Syrup | |
|---|---|
| Active ingredient | 0.25 g |
| Sorbitol Solution | 1.50 g |
| Glycerol | 2.00 g |
| Sodium Benzoate | 0.005 g |
| Flavour, Peach 17.42.3169 | 0.0125 ml |
| Purified Water q.s. to | 5.00 ml |

The active ingredient is dissolved in a mixture of the glycerol and most of the purified water. An aqueous solution of the sodium benzoate is then added to the solution, followed by addition of the sorbitol solution and finally the flavour. The volume is made up with purified water and mixed well.

| Formulation B | |
|---|---|
| Active ingredient | 0.125 g |
| Sterile, pyrogen-free, pH 7 phosphate buffer, q.s. to | 25 ml |

EXAMPLE 11

| Suppository | |
|---|---|
|  | mg/suppository |
| Active ingredient (63 μm)* | 250 |
| Hard Fat, B.P. (Witepsol H15 - Dynamit NoBel) | 1770 |
|  | 2020 |

*The active ingredient is used as a powder wherein at least 90% of the particles are of 63 μm diameter or less.

One-fifth of the Witepsol H15 is melted in a steam-jacketed pan at 45° C. maximum. The active ingredient is sifted through a 200 μm sieve and added to the molten base with mixing, using a Silverson fitted with a cutting head, until smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, allowed to cool to 40° C. At a temperature of 38° C. to 40° C., 2.0 g of the mixture is filled into suitable 2 ml plastic moulds. The suppositories are allowed to cool to room temperature.

EXAMPLE 12

| Pessaries | |
|---|---|
|  | mg/pessary |
| Active ingredient (63 μm) | 250 |
| Anhydrate Dextrose | 380 |
| Potato Starch | 363 |
| Magnesium Stearate | 7 |
|  | 1000 |

The above ingredients are mixed directly and pessaries prepared by direct compression of the resulting mixture.

EXAMPLE 13

Antiviral Activity for Hepatitis B Virus

Anti-HBV activity of compounds of formula (I) was determined using a method described by Korba B. E. and Milman G., Antiviral Research, 1991, Vol.15, pp217–228.

The assay utilises the human HBV producer cell line of HepG2, 2.2.15, described and characterized by Sells et al., PNAS 84, 1005 (1987) and J. Virol. 62, 2836 (1988), has been shown to share many characteristics of the HBV chronically infected hepatocyte. It is infectious as demonstrated by the ability to cause disease in chimpanzees. This cell line was utilized in vitro to identify compounds with anti-HBV activity.

To test compounds for antiviral activity, monolayer cultures were treated with the compound (50–200 μM), for 9 days. Supernatant media containing extracellular virion DNA (Dane particles) were harvested on days 0, 4 and 9, treated with proteinase K (1 mg/mL) and sodium dodecyl sulfate (1%), and incubated at 50° C. for one hour. DNA was extracted with equal volumes of phenol followed by chloroform and then precipitated using ammonium acetate and propanol. The DNA precipitate was dissolved and collected on nitrocellulose using the procedure of Schleicher and Schuell (S & S, 10 Optical Ave., Keene, N.H. 03431, Publication 700, 1987), and treated as described by Southern in J. Mol. Biol. 98, 503 (1975). Cells were harvested and the intracellular DNA obtained after cell lysis with guanidine isothiocyanate. The intracellular DNA was handled in the same manner as the extracellular DNA. After precipitation by ammonium acetate and propanol, the intracellular DNA precipitate was dissolved, cut by restriction endonuclease, Hind III, applied to agarose gel and then treated as described by Southern to determine the quantity of replicative intermediate forms. The antiviral effect of the drug was determined by measuring at least a 100-fold reduction in the amount of Dane particles extruded into the culture medium and a similar decrease in the intracellular replicative intermediates.

| | Extracellular HBV DNA (pg/ml. culture medium) | | |
|---|---|---|---|
| | Day 0 | Day 4 | Day 9 |
| Untreated Cells | 75 | 98 | 74 |
| | 70 | 49 | 73 |
| | 73 | 110 | 78 |
| | 72 | 110 | 95 |
| Treated | | | |
| Example | | | |
| 1   (100 µm) | 35 | 10 | 1 |
| | 83 | 7 | 0 |
| | 77 | 5 | 0 |
| | 75 | 16 | 1 |
| 3   (100 µm) | 59 | 13 | 0 |
| | 58 | 47 | 1 |
| | 55 | 36 | 0.1 |
| | 76 | 39 | 0 |
| 4   (24.8 µm) | 86 | 63 | 7 |
| | 53 | 41 | 1 |
| | 74 | 75 | 6 |
| | 65 | 59 | 6 |
| 5   (24.3 µm) | 95 | 43 | 14 |
| | 91 | 30 | 8 |
| | 86 | 49 | 3 |
| | 100 | 50 | 10 |

We claim:

1. A compound of formula (I)

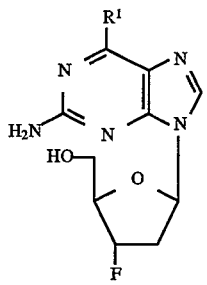

wherein $R^1$ represents a substituent selected from the group consisting of n-propoxy, cyclobutoxy, cyclopropylamino, piperidino, and pyrrolidino group; or a physiologically functional derivative thereof.

2. A compound according to claim 1 selected from:
2-Amino-9-(2,3-dideoxy-3-fluoro-β-D-erythro-pentofuranosyl)-6-n-propoxy-9H purine;
2-Amino-6-cyclobutoxy-9-(2,3-dideoxy-3-fluoro-β-D-erythro-pentofuranosyl)-9H-purine;
2-Amino-6-(1-pyrrolidino)-9-(2,3-dideoxy-3-fluoro- β-D-erythro-pentofuranosyl)-9H-purine;
2-Amino-6-(1-piperidino)-9-(2,3-dideoxy-3-fluoro-β-D-erythro-pentofuranosyl)-9H-purine; and
physiologically functional derivatives thereof.

3. 2-Amino-6-(cyclopropylamino)-9-(2,3-dideoxy-3-fluoro-β-D-erythro-pentofuranosyl)-9H-purine or a physiologically functional derivative thereof.

4. 2-amino-6-(1-pyrrolidino)-9-(2,3-dideoxy-3-fluoro-β, D-erthropentofuranosyl)-9H-purine or a physiologically functional derivative thereof.

5. A physiologically functional derivative of a compound of formula (I) according to any one of claims 1 to 3.

6. A derivative according to claim 5 selected from the group consisting of carboxylic acid esters, sulphonate esters, amino acid esters, mono- di- or triphosphate esters and salts.

7. A pharmaceutical formulation comprising a compound according to any one of claims 1 to 3 or 4, together with a pharmaceutically acceptable carrier therefor.

8. A formulation according to claim 7 in unit dosage form.

9. A formulation according to claim 8 in the form of a tablet or capsule.

10. A method of treatment or prevention of the symptoms or effects of a hepatitis B virus infection in an infected animal which comprises treating said animal with a therapeutically effective amount of a compound according to any one of claims 1 to 3 or 4.

11. A method according to claim 10 wherein the effective amount is from 0.5 to 120 mg per kg bodyweight per day.

12. A method according to claim 10 wherein the effective amount is 2 to 60 mg per kg bodyweight per day.

* * * * *